US010869799B2

(12) United States Patent
Yano et al.

(10) Patent No.: US 10,869,799 B2
(45) Date of Patent: Dec. 22, 2020

(54) OPERATING TABLE OPERATION DEVICE AND OPERATING TABLE

(71) Applicants: MEDICAROID CORPORATION, Kobe (JP); KAWASAKI JUKOGYO KABUSHIKI KAISHA, Kobe (JP); SYSMEX CORPORATION, Kobe (JP)

(72) Inventors: Yutaro Yano, Kobe (JP); Yoshiyuki Tamura, Kobe (JP); Mitsuichi Hiratsuka, Kobe (JP); Hiroaki Kitatsuji, Kobe (JP); Toru Mizumoto, Kobe (JP)

(73) Assignees: MEDICAROID CORPORATION, Kobe (JP); KAWASAKI JUKOGYO KABUSHIKI KAISHA, Kobe (JP); SYSMEX CORPORATION, Kobe (JP)

( * ) Notice: Subject to any disclaimer, the term of this patent is extended or adjusted under 35 U.S.C. 154(b) by 299 days.

(21) Appl. No.: 15/907,329

(22) Filed: Feb. 28, 2018

(65) Prior Publication Data

US 2018/0243152 A1    Aug. 30, 2018

(30) Foreign Application Priority Data

Feb. 28, 2017    (JP) ................. 2017-035606

(51) Int. Cl.
*A61G 13/04*    (2006.01)
*A61G 13/06*    (2006.01)
(Continued)

(52) U.S. Cl.
CPC ............ *A61G 13/04* (2013.01); *A61B 5/0555* (2013.01); *A61B 6/0407* (2013.01);
(Continued)

(58) Field of Classification Search
CPC ........ A61G 13/04; A61G 13/06; A61G 7/057; A61G 2203/16; A61G 2210/50;
(Continued)

(56) References Cited

U.S. PATENT DOCUMENTS 7,669,261 B2    3/2010    Früh et al.
7,860,550 B2    12/2010   Saracen et al.
(Continued)

FOREIGN PATENT DOCUMENTS

EP    1028684 B1    3/2004
JP    H06-071584 A    3/1994
(Continued)

OTHER PUBLICATIONS

The Japanese Office Action dated Jul. 2, 2019 in a counterpart Japanese patent application.
(Continued)

*Primary Examiner* — Bao Long T Nguyen
(74) *Attorney, Agent, or Firm* — Metrolex IP Law Group, PLLC

(57) ABSTRACT

An operation device according to one or more embodiments may include: a display; a move operation receiving unit that receives, from a user, a move operation to move a table on which a patient can be placed of an operating table; and an operation controller. In a condition in which the table is put in a tilted posture in accordance with the move operation, the operation controller may cause the display to display an elapsed time in the tilted posture.

24 Claims, 8 Drawing Sheets

(51) Int. Cl.
*A61B 6/04* (2006.01)
*A61B 5/055* (2006.01)
*A61B 6/00* (2006.01)
*A61G 7/057* (2006.01)

(52) U.S. Cl.
CPC ............ *A61B 6/0487* (2020.08); *A61G 13/06* (2013.01); *A61B 6/4441* (2013.01); *A61G 7/057* (2013.01); *A61G 2203/14* (2013.01); *A61G 2203/16* (2013.01); *A61G 2203/20* (2013.01); *A61G 2203/42* (2013.01); *A61G 2210/50* (2013.01)

(58) Field of Classification Search
CPC ............ A61G 2203/20; A61G 2203/42; A61G 2203/14; A61G 13/02–04; A61G 2203/10–16; A61G 7/001; A61G 7/002–008; A61G 7/018; A61B 6/0457; A61B 6/0407; A61B 5/0555; A61B 6/4441; A61B 5/704; A61B 34/25; B25J 11/008
USPC ................ 5/601, 607; 700/257, 264; 901/50
See application file for complete search history.

(56) References Cited

U.S. PATENT DOCUMENTS

| | | | |
|---|---|---|---|
| 8,126,114 | B2 | 2/2012 | Naylor et al. |
| 8,160,205 | B2 | 4/2012 | Saracen et al. |
| 9,326,907 | B2 | 5/2016 | Marie |
| 2002/0111701 | A1* | 8/2002 | Borders .................. A61F 7/007 700/60 |
| 2007/0251011 | A1* | 11/2007 | Matta .................. A61G 13/0036 5/624 |
| 2008/0172789 | A1* | 7/2008 | Elliot ...................... G06F 19/00 5/616 |
| 2010/0275927 | A1* | 11/2010 | Saracen ............... A61N 5/1049 128/845 |
| 2015/0000038 | A1 | 1/2015 | Obi |
| 2015/0327818 | A1 | 11/2015 | Buck et al. |
| 2017/0333275 | A1* | 11/2017 | Itkowitz ................. A61B 34/30 |

FOREIGN PATENT DOCUMENTS

| | | |
|---|---|---|
| JP | 2001-095857 A | 4/2001 |
| JP | 2001-522648 A | 11/2001 |
| JP | 2009-131718 A | 6/2009 |
| JP | 2014-100301 A | 6/2014 |
| JP | 2016-054860 A | 4/2016 |
| JP | 2016-067692 A | 5/2016 |

OTHER PUBLICATIONS

The Japanese Office Action dated Mar. 12, 2019 in a counterpart Japanese patent application.

Japanese Office Action dated Jun. 2, 2020 for the corresponding Japanese Patent Application No. 2017-35606, with English translation.

Japanese Office Action "JPOA" dated Sep. 1, 2020 for the related Japanese Patent Application No. 2019-170428, with English translation.

* cited by examiner

HORIZONTAL MOVEMENT MODE (M42)          (M41)

OPERATE UP, DOWN, RIGHT, LEFT, OR DIAGONAL KEY

PITCH MODE (M12)          (M11)

OPERATE RIGHT OR LEFT KEY

SELECT ROTATION CENTER

OPERATING TABLE OPERATION DEVICE AND OPERATING TABLE

CROSS REFERENCE TO RELATED APPLICATIONS

This application claims priority from prior Japanese Patent Application No. 2017-035606 filed with the Japan Patent Office on Feb. 28, 2017, entitled "OPERATING TABLE OPERATION DEVICE AND OPERATING TABLE", the entire contents of which are incorporated herein by reference.

BACKGROUND

The disclosure relates to an operating table operation device and an operating table.

EP1028684B1 discloses an operating table and an operation device thereof, the operating table having functions capable of changing the height and tilt of a table on which a patient is placed in order to move the patient to a position at which a doctor can treat the patient easily. In the operation device disclosed in EP1028684B1, a display displays illustration of the operating table in accordance with an operation mode of the table, thereby allowing an operator to easily operate the operating table in accordance with the operation mode.

SUMMARY

An operation device according to one or more embodiments may include: a display; a move operation receiving unit that receives, from a user, a move operation to move a table on which a patient can be placed of an operating table; and an operation controller. In a condition in which the table is put in a tilted posture in accordance with the move operation, the operation controller may cause the display to display an elapsed time in the tilted posture.

An operating table according to one or more embodiments may include: a table on which a patient can be placed; a movement mechanism that moves the table; an operation device including a move operation receiving unit that receives, from a user, a move operation to move the table; a display; and a controller that controls the movement mechanism in accordance with the move operation received by the move operation receiving unit. In a condition in which the table is put in a tilted posture in accordance with the move operation, the controller may cause the display to display an elapsed time in the tilted posture.

DETAILED DESCRIPTION

Figure 1:
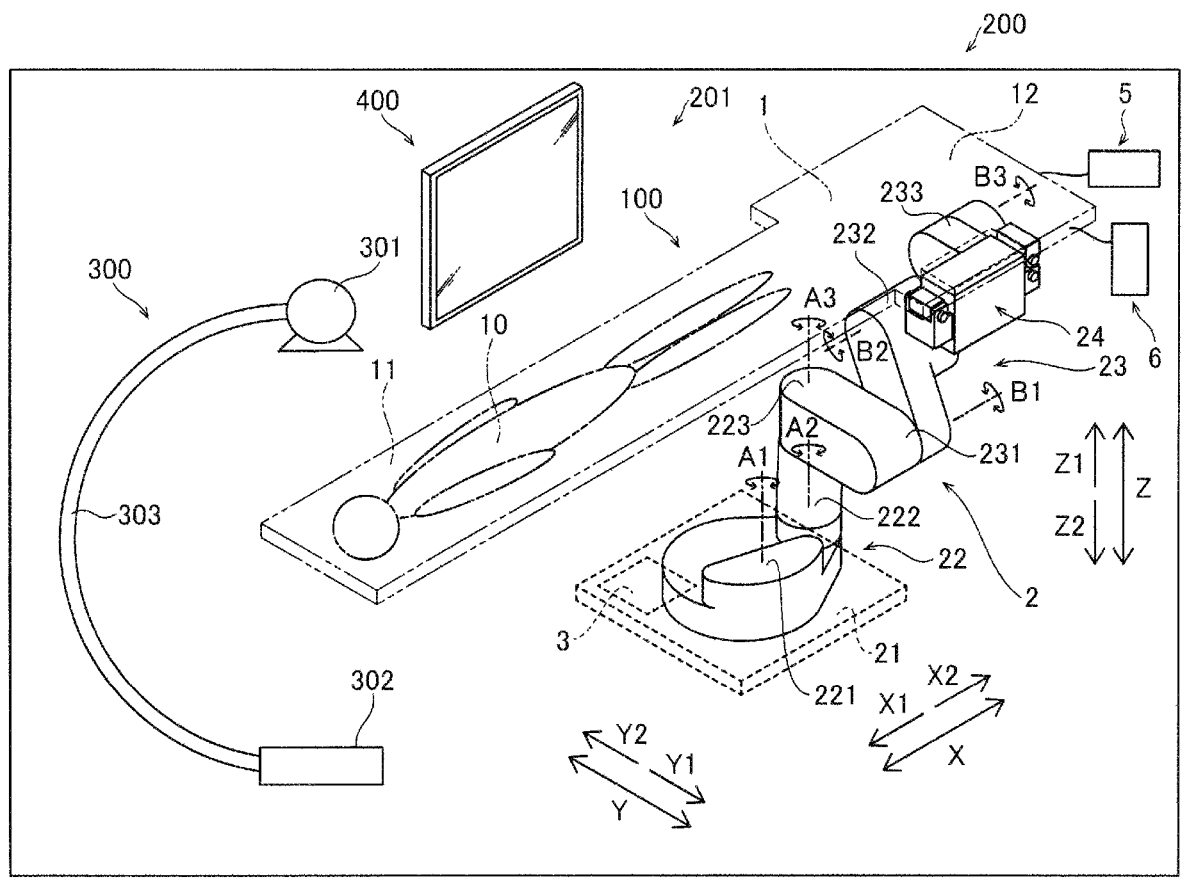
FIG. 1 is a diagram schematically illustrating a hybrid operation room including an operating table according to one or more embodiments.

Embodiments are described with reference to drawings, in which the same constituents are designated by the same reference numerals and duplicate explanation concerning the same constituents may be omitted for brevity and ease of explanation. The drawings are illustrative and exemplary in nature and provided to facilitate understanding of the illustrated embodiments and may not be exhaustive or limiting. Dimensions or proportions in the drawings may not be to scale, and are not intended to impose restrictions on the disclosed embodiments. For this reason, specific dimensions and the like should be interpreted with the accompanying descriptions taken into consideration. In addition, the drawings may include parts whose dimensional relationship and ratios are different from one drawing to another.

Prepositions, such as "on", "over" and "above" may be defined with respect to a surface, for example a layer surface, regardless of the orientation of the surface in space.

One or more embodiments will be described below with reference to the accompanying drawings.

(Configuration of Operating Table)

The following describes the configuration of an operating table 100 according to one or more embodiments with reference to FIGS. 1 to 7.

As illustrated in FIG. 1, the robotic operating table 100 is provided in a hybrid operation room 200. The hybrid operation room 200 is provided with a radiographic imaging apparatus 300 that captures a radiographic projection image of a patient 10. The hybrid operation room 200 may also be provided with a display 400 for displaying information on a surgical operation. In other words, the hybrid operation room 200 may be provided with a hybrid operation room system 201 including the robotic operating table 100 and the radiographic imaging apparatus 300. The display 400 may be suspended by, for example, an arm (not illustrated) and may be movable inside the hybrid operation room 200. The robotic operating table 100 is used as a table for a surgical operation performed in, for example, surgery or internal medicine. The robotic operating table 100 is capable of moving a table 1 to a placement position at which to place the patient 10 onto the table 1. Also, the robotic operating table 100 is capable of moving the patient 10 on the table 1 to, for example, a patient receiving position, an anesthetization position, a surgical operation position, a test position, a treatment position, a radiographic imaging position, and a patient passing position. The robotic operating table 100 is also capable of tilting the patient 10 on the table 1.

The robotic operating table 100 includes: the table 1 or a patient placement table on which a patient can placed, positioned or lies; an articulated robotic arm 2 (hereinafter referred to as a robotic arm 2); a controller 3; an operation device 5; and an operation device 6. The table 1 includes a radiolucent part 11 and a support unit 12 supporting the radiolucent part 11. The robotic arm 2 includes a base 21, a horizontal articulated assembly 22, a vertical articulated assembly 23, and a pitch mechanism 24. The horizontal articulated assembly 22 includes horizontal joints 221, 222 and 223. The vertical articulated assembly 23 includes vertical joints 231, 232 and 233. The radiographic imaging apparatus 300 includes an X-ray irradiation unit 301, an X-ray detection unit 302, and a C-arm 303. The robotic arm 2 is an example of "movement mechanism" in one or more recited embodiments. The operation devices 5 and 6 are each an example of "operating table operation device" in one or more recited embodiments. The horizontal joints 221 to 223 and the vertical joints 231 to 233 may be examples of "joint" in one or more recited embodiments.

Figure 2:
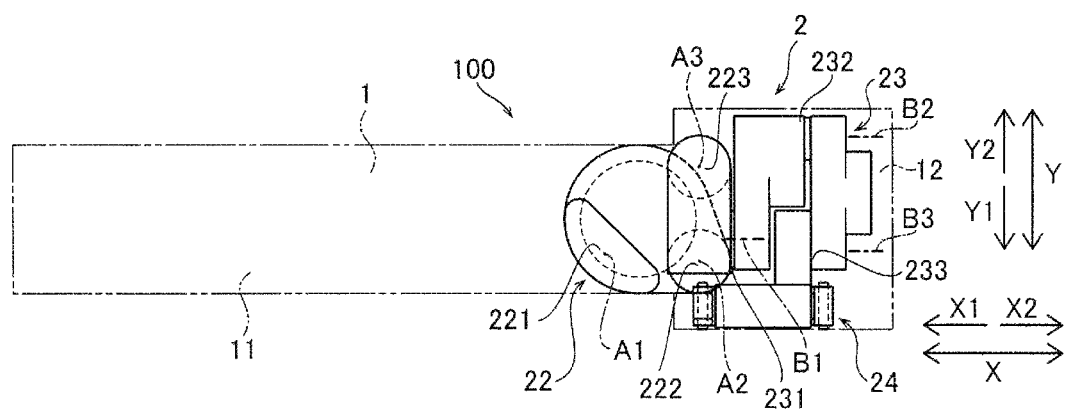
FIG. 2 is a plan view illustrating an operating table according to one or more embodiments.

As illustrated in FIGS. 1 and 2, the table 1 has a substantially rectangular flat plate shape. The table 1 has a substantially flat upper surface. The longitudinal direction of the table 1 is aligned with an X direction, and the transverse or widthwise direction of the table 1 is aligned with a Y direction. The table 1 is rotatable about an axis extending in a vertical direction (Z direction). In this example, the X direction is defined to be a horizontal direction along the longitudinal direction of the table 1, and the Y direction is defined to be a horizontal direction along the transverse direction of the table 1. Thus, the X direction and the Y direction are directions with reference to the table 1.

As illustrated in FIG. 1, the patient 10 is placed, positioned or lies on the radiolucent part 11 of the table 1. The radiolucent part 11 is disposed on an X1 direction side of the table 1. The radiolucent part 11 has a substantially rectangular shape. The radiolucent part 11 may be made of an X-ray transmittable material. The radiolucent part 11 may be made of, for example, a carbon material (graphite). The radiolucent part 11 may be made of, for example, carbon fiber reinforcement plastic (CFRP). With this configuration, a radiographic image of the patient 10 may be captured while the patient 10 is placed on the radiolucent part 11.

The support unit 12 of the table 1 is connected with the robotic arm 2. The support unit 12 is disposed on an X2 direction side of the table 1. The support unit 12 has a substantially rectangular shape. The support unit 12 supports the radiolucent part 11. The support unit 12 may be made of a material having an X-ray transmissivity smaller than that of the radiolucent part 11. The support unit 12 may be made of, for example, metal. The support unit 12 may be made of, for example, a steel material or an aluminum material.

The table 1 is moved by the robotic arm 2. Specifically, the table 1 is movable in the X direction along a horizontal direction, the Y direction along a horizontal direction orthogonal to the X direction, and the Z direction along a vertical direction orthogonal to the X direction and the Y direction. The table 1 may freely rotate (roll) about an axis extending in the X direction. The table 1 may also freely rotate (pitch) about an axis extending in the Y direction. The table 1 may also freely rotate (yaw) about an axis extending in the Z direction.

The robotic arm 2 moves the table 1. As illustrated in FIG. 1, the robotic arm 2 has one end supported by the base 21 fixed to the floor, and the opposite end supporting the table 1. Specifically, the robotic arm 2 is supported by the base 21 to be rotatable about a base rotation axis (rotation axis A1) substantially perpendicular to an installation surface on which the base 21 is installed. The robotic arm 2 supports the vicinity of one end of the table 1 on the X2 direction side in the longitudinal direction (X direction). In other words, the opposite end of the robotic arm 2 supports the support unit 12 at the vicinity of the one end of the table 1.

The robotic arm 2 is capable of moving the table 1 with seven degrees of freedom. Specifically, the horizontal articulated assembly 22 provides the robotic arm 2 with three degrees of freedom: to rotate about the rotation axis A1 extending in the vertical direction; to rotate about a rotation axis A2 extending in the vertical direction; and to rotate about a rotation axis A3 extending in the vertical direction. In addition, the vertical articulated assembly 23 provides the robotic arm 2 with three degrees of freedom: to rotate about a rotation axis B1 extending in the horizontal direction; to rotate about a rotation axis B2 extending in the horizontal direction; and to rotate about a rotation axis B3 extending in the horizontal direction. In addition, the pitch mechanism 24 provides the robotic arm 2 with one degree of freedom to pitch the table 1 about a rotation axis extending in the transverse direction (Y direction).

The base 21 is buried and fixed in the floor. The base 21 is provided substantially at the center of a movement range of the table 1 in plan view (when viewed in the Z direction).

Figure 3:
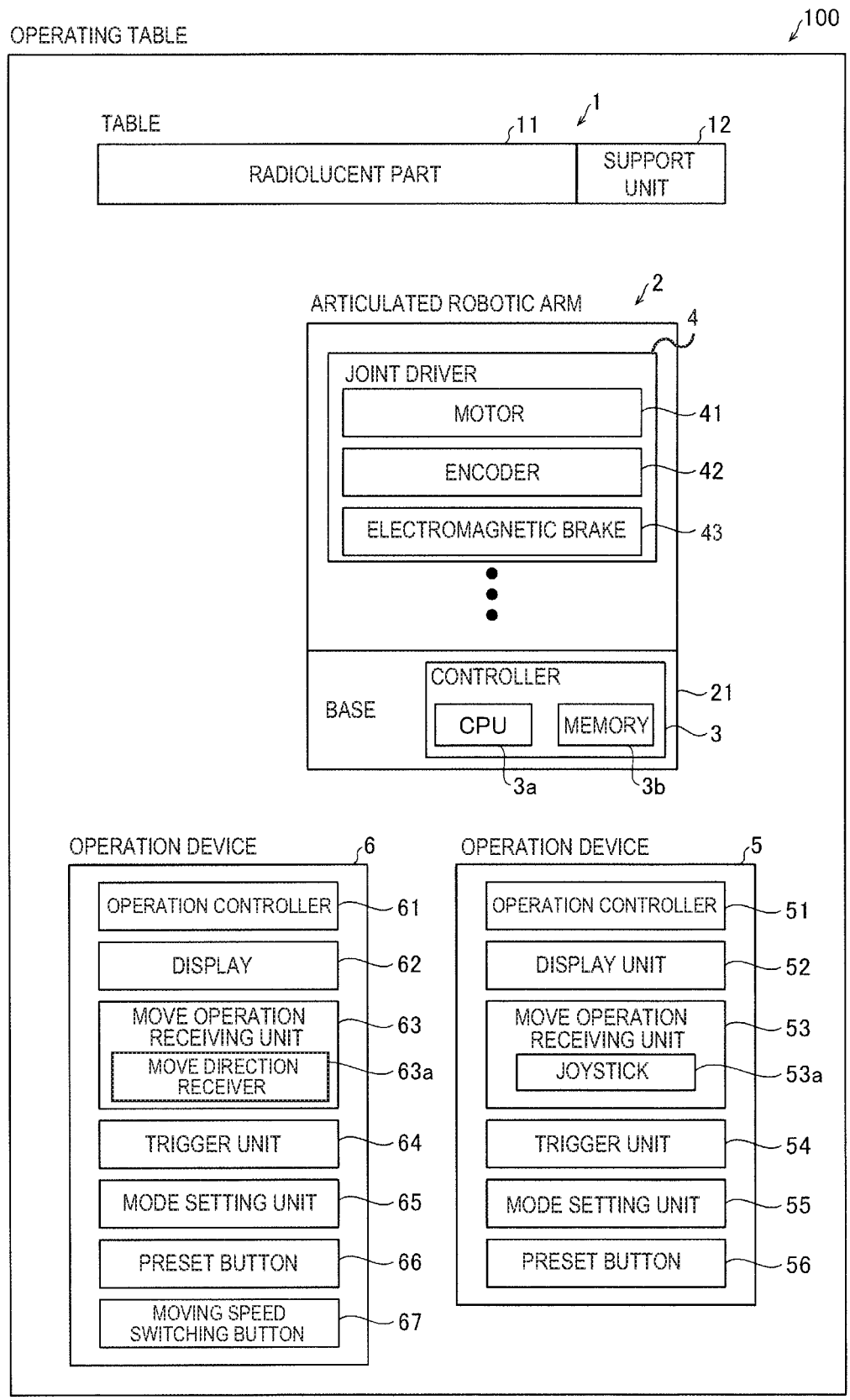
FIG. 3 is a block diagram illustrating an operating table according to one or more embodiments.

As illustrated in FIG. 3, the horizontal joints 221 to 223 and the vertical joints 231 to 233 are each provided with a joint driver 4. The horizontal joints 221 to 223 and the vertical joints 231 to 233 are each driven by the joint driver 4 thus provided. The joint driver 4 includes a motor 41, an encoder 42, an electromagnetic brake 43, and a decelerator (not illustrated). The horizontal joints 221 to 223 and the vertical joints 231 to 233 are each rotated about a rotation axis through drive of the motor 41.

The motor 41 includes a servomotor. The motor 41 is driven under control of the controller 3. The electromagnetic brake 43 brakes a joint (the horizontal joints 221 to 223 and the vertical joints 231 to 233). The encoder 42 detects a drive amount of the motor 41 and transmits a result of the detection to the controller 3. The electromagnetic brake 43 is a non-excitation actuation electromagnetic brake that brakes the motor 41 when the motor 41 is not energized. The electromagnetic brake 43 may be a built-in electromagnetic brake of the motor 41 or an electromagnetic brake externally connected with the motor 41.

As illustrated in FIG. 2, the robotic arm 2 is disposed entirely behind the table 1 in plan view (when viewed in the Z direction). For example, the robotic arm 2 is housed in a housing space below the table 1 when the table 1 is positioned at the surgical operation position. Specifically, the robotic arm 2 is folded completely behind the table 1 in plan view (when viewed in the Z direction) when the table 1 is moved to a position for a surgical operation or treatment on the patient 10 being placed on the table 1. When the robotic arm 2 is folded, the length of the robotic arm 2 in a direction parallel to the longitudinal direction of the table 1 is shorter than half of the length of the table 1 in the longitudinal direction.

The robotic arm 2 causes the table 1 to yaw about an axis extending in the vertical direction (Z direction) by using at least one horizontal joint (at least one of the joints 221, 222, and 223). The robotic arm 2 causes the table 1 to roll about an axis extending in the longitudinal direction (X direction) by using at least one vertical joint (at least one of the joints 231, 232, and 233). The robotic arm 2 causes the table 1 to pitch about an axis extending in the transverse direction (Y direction) by using the pitch mechanism 24.

Figure 4:
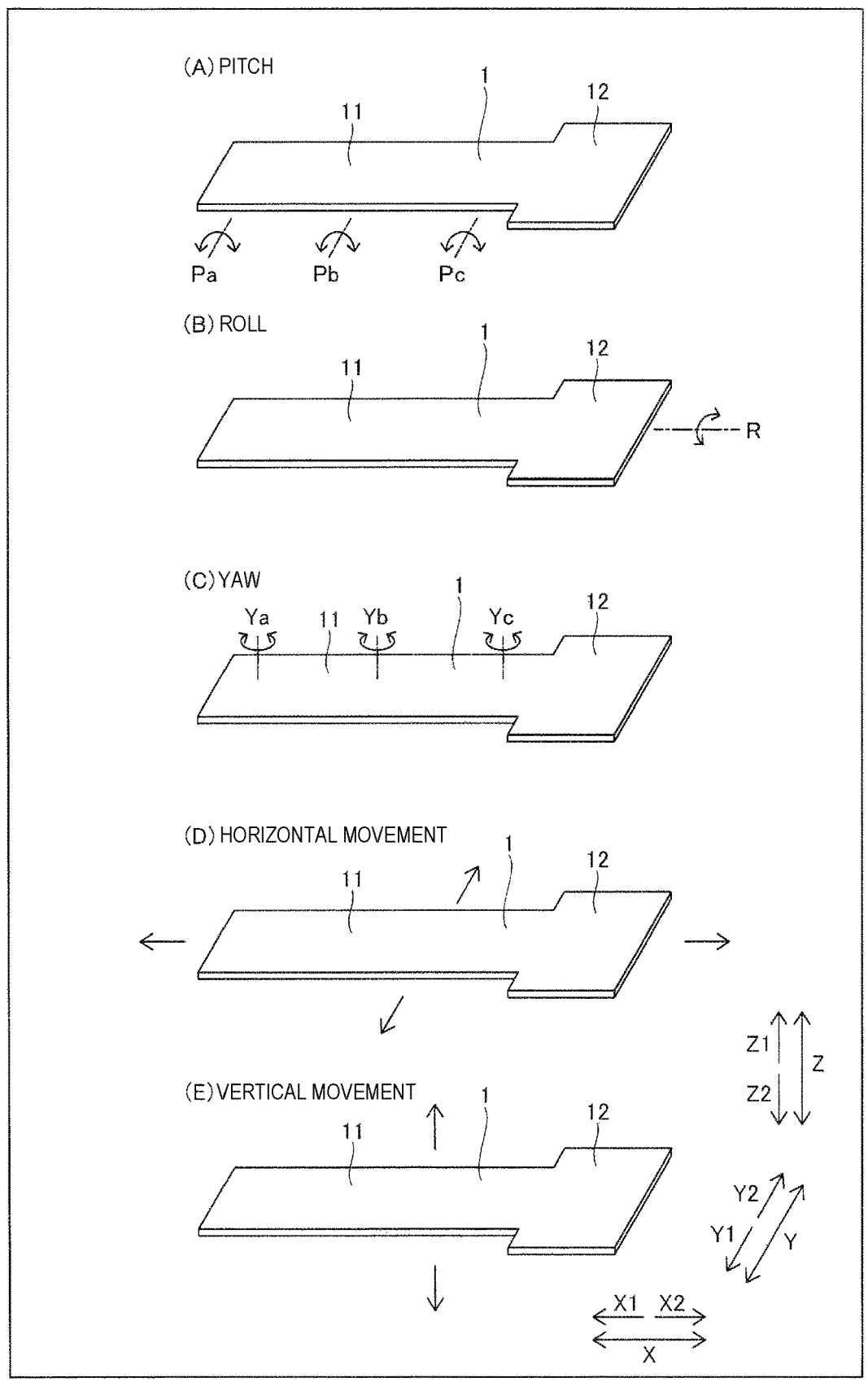
FIG. 4 is a diagram illustrating movement and posture change of a table of an operating table according to one or more embodiments.

Specifically, as illustrated in (A) of FIG. 4, the robotic arm 2 causes the table 1 to pitch about an axis Pa, Pb, or Pc parallel to the transverse direction (Y direction) of the table 1. As illustrated in (B) of FIG. 4, the robotic arm 2 causes the table 1 to roll about an axis R parallel to the longitudinal direction (X direction) of the table 1. As illustrated in (C) of FIG. 4, the robotic arm 2 causes the table 1 to yaw about an axis Ya, Yb, or Yc parallel to the vertical direction (Z direction).

As illustrated in (D) of FIG. 4, the robotic arm 2 moves the table 1 straight in a horizontal plane (in the XY plane). As illustrated in (E) of FIG. 4, the robotic arm 2 moves the table 1 upward and downward in the vertical direction (Z direction).

The controller 3 is a control circuit including, for example, a central processing unit (CPU) 3a, and a memory 3b. The memory 3b according to one or more embodiments may include such devices as a flash memory device, magnetic disk device such as a hard disk drive, and an optical disk device that reads data from a recording medium. In one or more embodiments, for example, the recording medium may include Blu-ray disk, CD-ROM (Compact Disk Read Only Memory), DVD (Digital Versatile Disk). memory The controller 3 is installed in the base 21 and controls movement of the table 1 by the robotic arm 2. Specifically, the controller 3 controls drive of the robotic arm 2 to move the table 1 based on an operation by a medical person (operator). The controller 3 acquires information on the posture of the robotic arm 2 and the position and posture of the table 1 based on an output from the encoder 42 of the motor 41 of each joint.

The operation devices 5 and 6 each receive an operation to move the table 1 by the medical person (operator). The operation devices 5 and 6 are provided to allow a user (medical person) to operate movement and posture change of the table 1 of the operating table 100 on which a patient can be placed. The operation devices 5 and 6 are each capable of performing an operation of the table 1. The operation device 5 is attached to the table 1 and used. The operation device 6 may be disposed at a position separate from the table 1. The operation devices 5 and 6 are attached to the table 1 through engagement with engagement members provided on side surfaces of the support unit 12 of the table 1. The operation devices 5 and 6 are connected with the controller 3 through wired communication.

Figure 5:
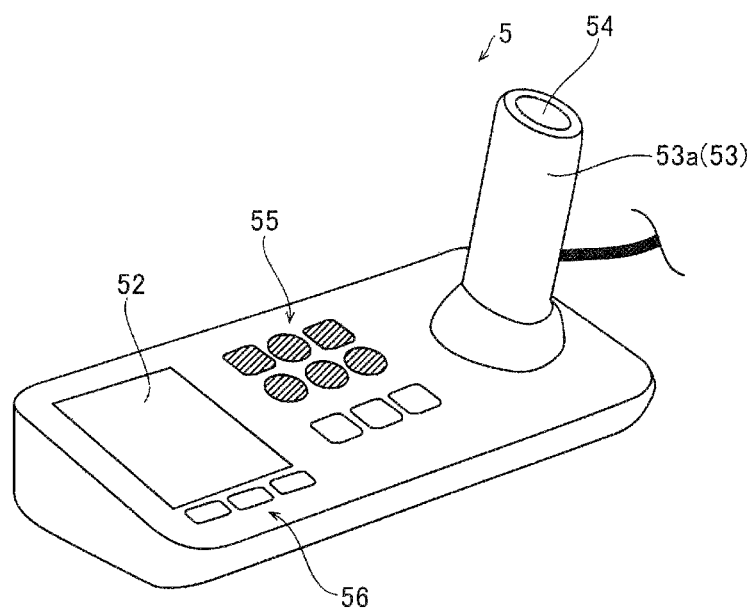
FIG. 5 is a perspective view illustrating an operation device of an operating table according to one or more embodiments, which includes a joystick.
Figure 6:
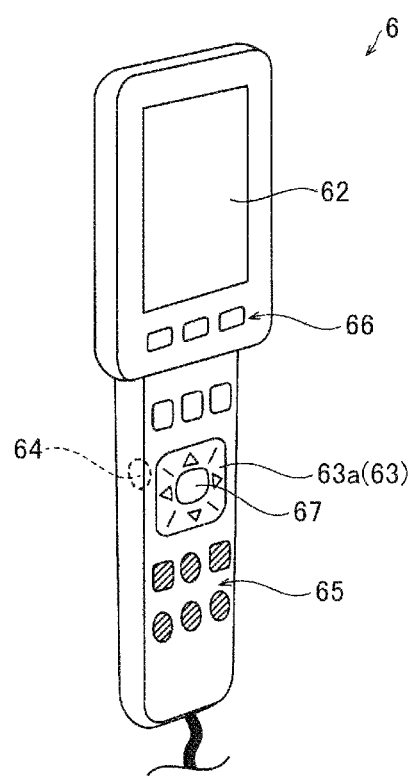
FIG. 6 is a perspective view illustrating an operation device of an operating table according to one or more embodiments, which includes a move direction receiver.

As illustrated in FIGS. 3 and 5, the operation device 5 includes an operation controller 51, a display 52, a move operation receiving unit 53 including a joystick 53a, a trigger unit 54, a mode setting unit 55, and a preset button 56. As illustrated in FIGS. 3 and 6, the operation device 6 includes an operation controller 61, a display 62, a move operation receiving unit 63 including move direction receivers 63a, a trigger unit 64, a mode setting unit 65, a preset button 66, and a moving speed switching button 67.

The operation controller 51 (61) controls each component of the operation device 5 (6) based on an operation by the medical person (operator). Specifically, the operation controller 51 (61) causes the display 52 (62) to display an image based on an operation by the medical person (operator). The operation controller 51 (61) transmits operation information to the controller 3 based on an operation by the medical person (operator).

In one or more embodiments, in a condition in which the table 1 is put in a tilted posture, the operation controller 51 (61) causes the display 52 (62) to display an elapsed time in the tilted posture. The operation controller 51 (61) also causes the display 52 (62) to display posture information of the table 1.

The display 52 (62) displays, for example, the state of the table 1, the state of an operation of the operation device 5 (6), and an operation screen. The display 52 (62) includes a display, such as a liquid crystal display or an organic electroluminescence (EL) display. In the hybrid operation room 200, the controller 3 of the robotic operating table 100, the operation controller 51 (61) of the operation device 5 (6), and the display 400 (refer to FIG. 1) are connected with each other to perform communication therebetween. The display 400 is capable of displaying, for example, the state of the table 1, the state of an operation of the operation device 5 (6), and the operation screen. The display 400 is capable of displaying, for example, an image displayed by the display 52 (62) of the operation device 5 (6). With this configuration, in the hybrid operation room 200, the operation state of the robotic operating table 100 may be checked by medical persons all at once. Specifically, when the table 1 is put in a tilted posture, the controller 3 or the operation controller 51 (61) causes the display 400 to display an elapsed time in the tilted posture. The controller 3 or the operation controller 51 (61) also causes the display 400 to display posture information of the table 1. The display 400 may be an input and display including a touch panel to receive, from a medical person (user) through an operation on a screen, an operation to move the table 1.

In one or more embodiments, the display 52 (62) displays, as posture information of the table 1, a diagram (illustration) representing the posture of the table 1. The display 52 (62) also displays, as posture information of the table 1, the tilt angle of the table 1 with respect to a horizontal plane. The display 52 (62) also displays, as posture information of the table 1, a diagram (illustration) including arrows indicating directions of rotation of the table 1 with respect to a horizontal plane, and a tilt angle of the table 1 with respect to the horizontal plane.

The move operation receiving unit 53 (63) receives, from a user (medical person), a move operation to move the table 1. The move operation receiving unit 53 (63) receives, from a user (medical person), a posture change operation to change the posture of the table 1. The move operation receiving unit 53 of the operation device 5 includes the joystick 53a. The joystick 53a is operated by being tilted. The joystick 53a receives an operation to move the table 1 in accordance with the direction and angle of the tilt. The move operation receiving unit 63 of the operation device 6 includes the move direction receivers 63a for respective directions in which the table 1 is moved. The move direction receivers 63a are provided for eight directions, for example. Each move direction receiver 63a receives an operation to move the table 1 by being pressed.

The trigger unit 54 (64) is provided to enable the operation of the move operation receiving unit 53 (63). Specifically, energization of the motor 41 is turned on when the trigger unit 54 (64) is operated. With this configuration, braking of the motor 41 by the electromagnetic brake 43 is released by operating the trigger unit 54 (64). As a result, only while the trigger unit 54 (64) is operated, the operation of the move operation receiving unit 53 (63) is enabled, so that the table 1 can be moved. In the robotic operating table 100, energization of the motor 41 is turned off when the operation of the trigger unit 54 (64) is released. With this configuration, the motor 41 is braked by the electromagnetic brake 43 by releasing the operation of the trigger unit 54 (64). As a result, when the trigger unit 54 (64) is not operated, the operation of the move operation receiving unit 53 (63) is disabled, so that the table 1 cannot be moved.

The trigger unit 54 of the operation device 5 is provided at a leading end of the joystick 53a. In the operation device 5, the operation of the joystick 53a is enabled when the trigger unit 54 is pressed. The operation of the joystick 53a is disabled while the pressing on the trigger unit 54 is released. The trigger unit 64 of the operation device 6 is provided on a surface opposite to a surface on which the move direction receivers 63a are provided. In the operation device 6, the operation of the move direction receivers 63a is enabled when the trigger unit 64 is pressed. The operation of the move direction receivers 63a is disabled while the pressing on the trigger unit 64 is released.

The mode setting unit 55 (65) is capable of setting an operation mode of a movement and a posture change of the table 1. Specifically, the mode setting unit 55 (65) receives an operation mode change instruction by a user. The mode setting unit 55 (65) is provided to set an operation mode among operation modes. The mode setting unit 55 (65) is capable of setting, as the operation mode to move the table 1 and change a posture of the table 1, a pitch mode in which the table 1 is rotated about an axis parallel to the transverse direction (Y direction) of the table 1, a roll mode in which the table 1 is rotated about an axis parallel to the longitudinal direction (X direction) of the table 1, a yaw mode in which the table 1 is rotated in a horizontal plane about a rotation axis extending in the vertical direction (Z direction), a horizontal movement mode in which the table 1 is linearly moved in a horizontal plane, a vertical movement mode in which the table 1 is vertically moved, and a horizontal posture returning mode.

Figure 7A:
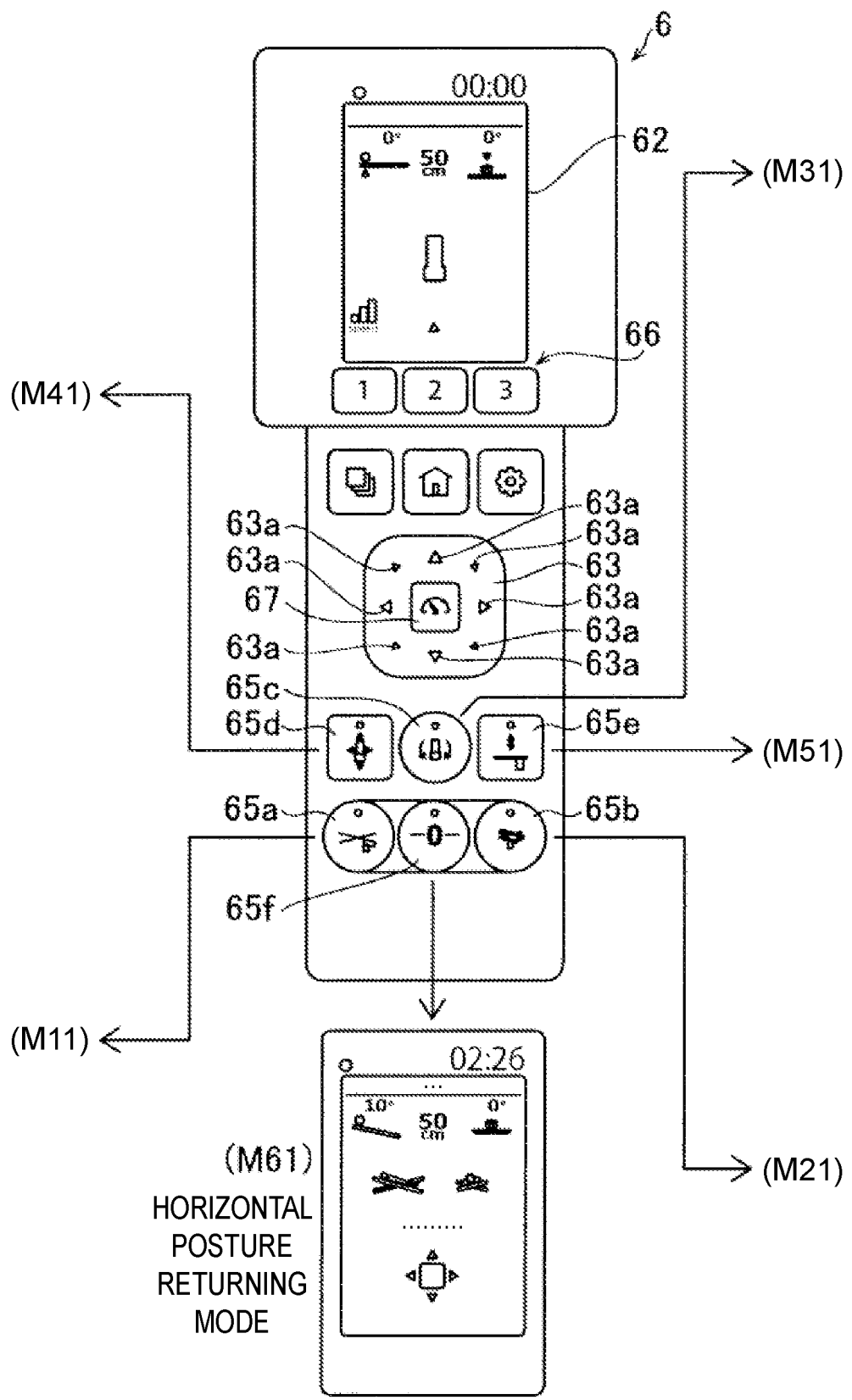
FIGS. 7A to 7C are diagrams illustrating a display of an operating table of according to one or more embodiments.
Figure 7B:
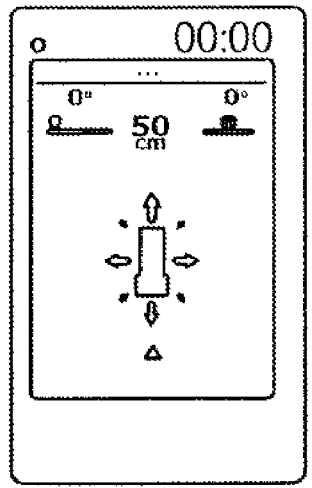
Figure 7B:
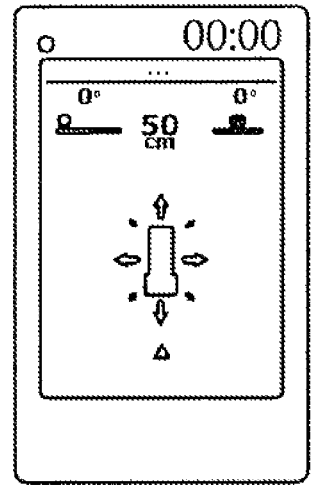
Figure 7B:
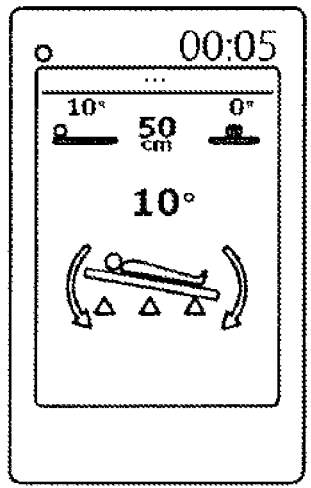
Figure 7B:
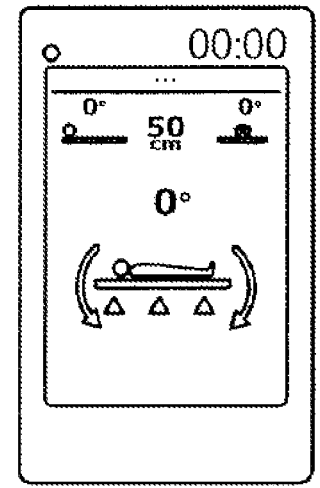
Figure 7C:
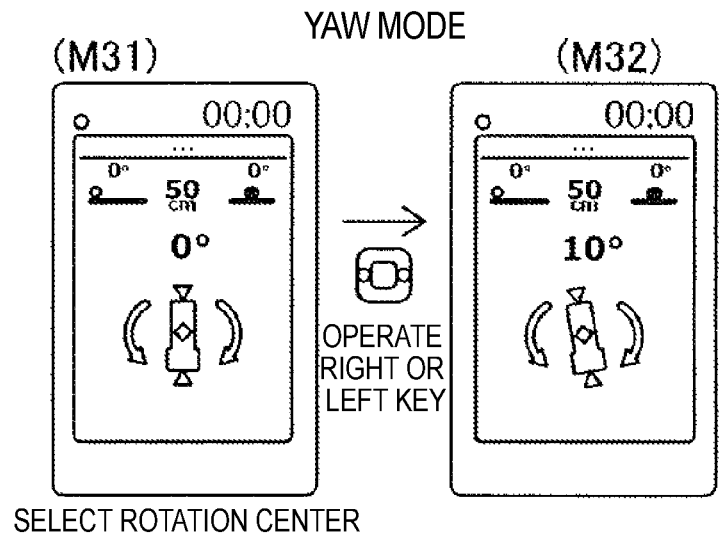
Figure 7C:
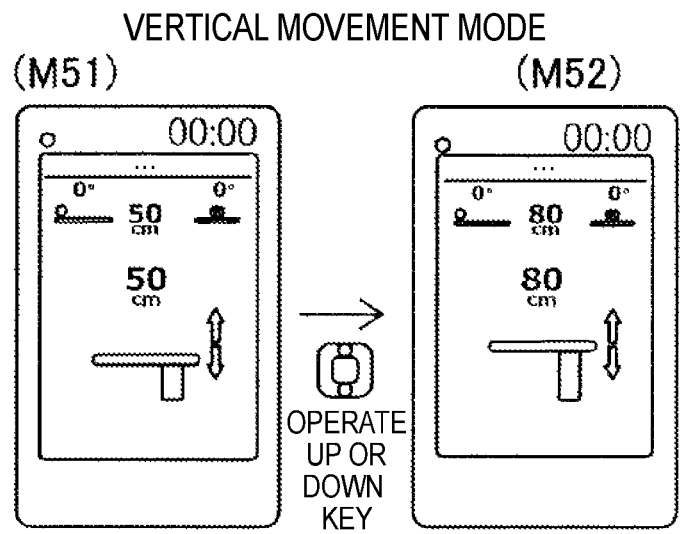
Figure 7C:
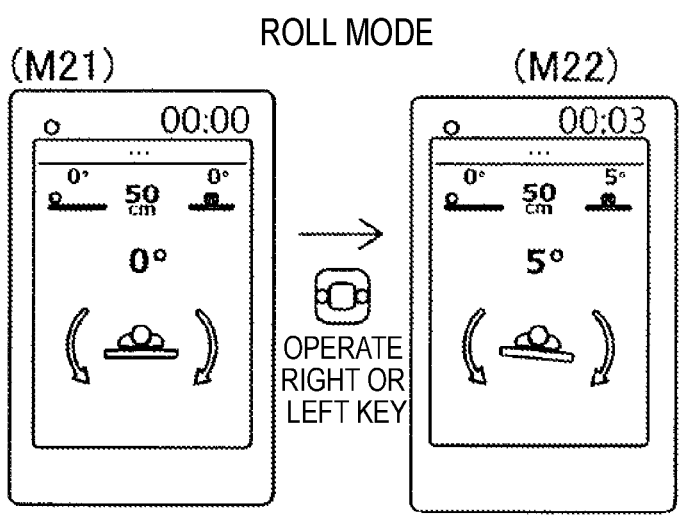

The mode setting unit 65 of the operation device 6 includes buttons for the respective modes. For example, as illustrated in FIGS. 7A to 7C, the mode setting unit 65 includes a pitch mode button 65a, a roll mode button 65b, a yaw mode button 65c, a horizontal movement mode button 65d, a vertical movement mode button 65e, and a horizontal posture returning mode button 65f. The mode setting unit 55 of the operation device 5 substantially includes the same buttons. When a mode is selected by pressing the corresponding button of the mode setting unit 55 (65), the pressed button lights up.

The table 1 is moved when the trigger unit 54 (64) and the move operation receiving unit 53 (63) are operated with the operation mode selected by the mode setting unit 55 (65). As illustrated in FIG. 5 (FIG. 6), the mode setting unit 55 (65) and the move operation receiving unit 53 (63) have background colors different from each other. In other words, the mode setting unit 55 (65) and the move operation receiving unit 53 (63) are distinguishable from each other by color tone.

As illustrated in FIG. 4, in the pitch mode, the position of the rotation center is selectable from among positions in the longitudinal direction (X direction) of the table 1. For example, in the pitch mode, the position of the rotation center is selectable from among the axis Pa adjacent to the head, the axis Pb adjacent to the abdominal part, and the axis Pc adjacent to the leg part. In the yaw mode, the position of the rotation center is selectable from among positions in the longitudinal direction (X direction) of the table 1. For example, in the yaw mode, the position of the rotation center is selectable from among the axis Ya adjacent to the head, the axis Yb adjacent to the abdominal part, and the axis Yc adjacent to the leg part.

The preset button 56 (66) is provided to set a preset position as a movement destination of the table 1 and register the current position of the table 1 as a preset position. When the current position of the table 1 is registered as a preset position by the preset button 56 (66), position information of the table 1 and posture information of the robotic arm 2 at that time are stored in the memory 3b of the controller 3. When the trigger unit 54 (64) and the move operation receiving unit 53 (63) are operated with a preset position selected by the preset button 56 (66), the table 1 is moved to the selected preset position. For example, the patient receiving position, the anesthetization position, the surgical operation position, the test position, the treatment position, the radiographic imaging position, and the patient passing position are registered as preset positions. The preset positions are registered separately for each operative procedure of a surgical operation. Position information of the table 1 at a registered preset position and posture information of the robotic arm 2 at that time are stored in the memory 3b of the controller 3.

The controller 3 controls drive of the robotic arm 2 to move the table 1 while the trigger unit 54 (64) and the move operation receiving unit 53 (63) are operated together. Meanwhile, when the table 1 arrives at the preset position, i.e., the position after the movement, the controller 3 performs control that invalidates the operation of the move operation receiving unit 53 (63) and stops the movement of the table 1. Then, when a user stops the operation of the trigger unit 54 (64), the controller 3 performs control that stops energization of the motor 41 and actuates the electromagnetic brake 43. In this way, the table 1 and the robotic arm 2 are fixed at the preset position immediately. The controller 3 may notify the user of the arrival at the preset position.

The moving speed switching button 67 is provided to change the moving speed of the table 1. The moving speed of the table 1 is switched at stages at each press on the moving speed switching button 67. For example, the moving speed of the table 1 is switchable between moving speeds at three stages.

In one or more embodiments, when the pitch mode is set, the operation controller 51 (61) causes the display 52 (62) to display, as posture information of the table 1, a diagram (illustration) including arrows indicating directions of rotation of the table 1 with respect to a horizontal plane and an angle of the table 1 with respect to the horizontal direction. For example, as illustrated in FIGS. 7A to 7C, in the pitch mode, the display 62 (52) displays a screen for selecting the position of the rotation center at M11. The display 62 (52) also displays a diagram including arrows indicating the directions of rotation with respect to the horizontal plane. In the pitch mode, the table 1 is caused to pitch by operating a right or left key of the move operation receiving unit 63. In the case of the joystick 53a, the table 1 is caused to pitch by tilting the joystick 53a to the right or left. When the table 1 is caused to pitch, the tilt angle of the table 1 with respect to the horizontal plane is displayed at M12. When the table 1 is stopped in a tilted state, an elapsed time during which the table 1 is in a tilted posture is displayed. Although FIGS. 7A to 7C illustrates an example with the operation device 6, the same operations can substantially be performed with the operation device 5, and the same display is performed by the display 52.

When the roll mode is set, the operation controller 51 (61) causes the display 52 (62) to display, as posture information of the table 1, a diagram (illustration) including arrows indicating directions of rotation of the table 1 with respect to the horizontal plane and an angle of the table 1 with respect to the horizontal direction. For example, as illustrated in FIGS. 7A to 7C, in the roll mode, the display 62 (52) displays a diagram including arrows indicating the directions of rotation with respect to the horizontal plane at M21. In the roll mode, the table 1 is caused to roll by operating a right or left key of the move operation receiving unit 63. In the case of the joystick 53a, the table 1 is caused to roll by tilting the joystick 53a to the right or left. When the table 1 is caused to roll, the tilt angle of the table 1 with respect to the horizontal plane is displayed at M22. When the operation of the move operation receiving unit 63 or the joystick 53a is stopped with the table 1 tilted, the table 1 is stopped. Then, when the operation of the trigger unit 64 (54) is stopped in this state, energization of the motor 41 is stopped, the electromagnetic brake 43 is actuated, and an elapsed time during which the table 1 is held in a tilted posture is displayed.

When the table 1 is put in a tilted posture in the pitch mode and the roll mode, the actuation of the motor 41 is stopped by turning off the operation of the trigger unit 64 (54), and counting of the elapsed time in the tilted posture is started in response to the actuation of the electromagnetic brake 43. Specifically, the operation controller 51 (61) starts counting of the elapsed time during which the table 1 is held in the tilted posture in response to a stop signal of the motor 41 from the controller 3. The operation controller 51 (61) resets counting of the elapsed time during which the table 1 is held in the tilted posture in response to an operation signal of the motor 41 from the controller 3. The operation controller 51 (61) may start counting of the elapsed time during which the table 1 is held in the tilted posture when the operation of the trigger unit 64 (54) is turned off.

When the yaw mode is set, the operation controller 51 (61) causes the display 52 (62) to display, as posture information of the table 1, a diagram (illustration) including arrows indicating directions of rotation of the table 1 with respect to a reference position and an angle of the table 1 with respect to the reference position. For example, as illustrated in FIGS. 7A to 7C, in the yaw mode, the display 62 (52) displays a screen for selecting the position of the rotation center at M31. The display 62 (52) also displays a diagram including arrows indicating the directions of rotation in plan view. In the yaw mode, the table 1 is caused to yaw by operating a right or left key of the move operation receiving unit 63. In the case of the joystick 53a, the table 1 is caused to yaw by tilting the joystick 53a to the right or left. When the table 1 is caused to yaw, the tilt angle of the table 1 with respect to the reference position is displayed at M32.

When the horizontal movement mode is set, the operation controller 51 (61) causes the display 52 (62) to display, as posture information of the table 1, a diagram (illustration) including arrows indicating moving directions of the table 1. For example, as illustrated in FIGS. 7A to 7C, in the horizontal movement mode, the display 62 (52) displays a diagram including arrows indicating the moving directions in plan view at M41. In the horizontal movement mode, the table 1 is moved in a horizontal plane by operating an up, down, right, left, or diagonal key of the move operation receiving unit 63. In the case of the joystick 53a, the table 1 is moved in a horizontal plane by a tilting operation in an up, down, right, left, or diagonal direction.

When the vertical movement mode is set, the operation controller 51 (61) causes the display 52 (62) to display, as posture information of the table 1, a diagram (illustration) including arrows indicating directions of vertical movement of the table 1 and a height of the table 1 from a floor surface. For example, as illustrated in FIGS. 7A to 7C, in the vertical movement mode, the display 62 (52) displays a diagram including arrows indicating the directions of upward and downward movements at M51. In the vertical movement mode, an upward or downward movement of the table 1 is performed by operating an up or down key of the move operation receiving unit 63. In the case of the joystick 53a, the upward or downward movement of the table 1 is performed by tilting the joystick 53a upward or downward. When the upward or downward movement of the table 1 is performed, the height position of the table 1 with respect to the floor surface is displayed at M52.

When the horizontal posture returning mode is set, the operation controller 51 (61) causes the display 52 (62) to display an operation display for returning the table 1 to a horizontal posture. For example, as illustrated in FIGS. 7A to 7C, in the horizontal posture returning mode, the display 62 (52) displays a display "Table will return to the horizontal posture. Press a movement button" at M61. In the horizontal posture returning mode, the table 1 tilted with respect to the horizontal plane through the pitch mode and the roll mode is moved so that the table 1 becomes parallel to the horizontal plane.

The operation controller 51 changes the moving speed of the table 1 in accordance with a tilt at which the joystick 53a is operated. Specifically, the operation controller 51 sets a lower moving speed for a smaller tilt of the joystick 53a and sets a higher moving speed for a larger tilt of the joystick 53a.

The controller 3 performs control to move the table 1 while at least one of the move direction receivers 63a is operated. Specifically, the controller 3 controls drive of the robotic arm 2 to move the table 1 while at least one of the move direction receivers 63a is operated. Accordingly, if the operation device 6 is enabled to receive an operation by a medical person (operator), the table 1 is moved only while at least one of the move direction receivers 63a is operated.

The controller 3 performs control to move the table 1 while the joystick 53a is operated. Specifically, the controller 3 controls drive of the robotic arm 2 to move the table 1 while the joystick 53a is operated. Accordingly, if the operation device 5 receives an operation by a medical person (operator), the table 1 is moved only while the joystick 53a is operated.

The controller 3 controls drive of the robotic arm 2 to move the table 1 while the trigger unit 54 (64) and the move operation receiving unit 53 (63) are operated together. Accordingly, if the operation device 5 receives an operation by a medical person (operator), the table 1 is moved only while the operation of pressing the trigger unit 54 and the operation of tilting the joystick 53a are performed together. If the operation device 6 receives an operation by a medical person (operator), the table 1 is moved only while the operation of pressing the trigger unit 64 and the operation of pressing any of the move direction receivers 63a are performed together.

(Configuration of Radiographic Imaging Apparatus)

Hereinafter, the configuration of the radiographic imaging apparatus 300 is described with reference to FIG. 1.

As illustrated in FIG. 1, the radiographic imaging apparatus 300 is capable of capturing a radiographic projection image of the patient 10 being placed on the table 1. The X-ray irradiation unit 301 and the X-ray detection unit 302 are supported by the C-arm 303. The X-ray irradiation unit 301 and the X-ray detection unit 302 are moved along with movement of the C-arm 303 and disposed facing to each other on both sides of the patient 10 at the imaging position at radiographic imaging. For example, one of the X-ray irradiation unit 301 and the X-ray detection unit 302 is disposed in a space above the table 1, and the other is disposed in a space below the table 1. At radiographic imaging, the C-arm 303 supporting the X-ray irradiation unit 301 and the X-ray detection unit 302 is disposed in the spaces above and below the table 1.

The X-ray irradiation unit 301 is disposed facing to the X-ray detection unit 302. The X-ray irradiation unit 301 is capable of emitting X-ray toward the X-ray detection unit 302. The X-ray detection unit 302 detects the X-ray emitted by the X-ray irradiation unit 301. The X-ray detection unit 302 includes a flat panel detector (FPD). The X-ray detection unit 302 captures a radiographic image based on detected X-ray. Specifically, the X-ray detection unit 302 converts detected X-ray into an electric signal and transmits the electric signal to an image processing unit (not illustrated).

The C-arm 303 has one end connected with the X-ray irradiation unit 301 and the opposite end connected with the X-ray detection unit 302. The C-arm 303 has a substantially C shape. With this configuration, at radiographic imaging, the C-arm 303 can support the X-ray irradiation unit 301 and the X-ray detection unit 302 while extending around the table 1 and the patient 10 to avoid interference therewith. The C-arm 303 is movable relative to the table 1. Specifically, the C-arm 303 is movable in the horizontal direction and the vertical direction to dispose the X-ray irradiation unit 301 and the X-ray detection unit 302 at desired positions relative to the patient 10 being placed on the table 1, and is also rotatable about a rotation axis extending in the horizontal direction and a rotation axis extending in the vertical direction. The C-arm 303 is moved by a drive unit (not illustrated) based on an operation by a medical person (operator). The C-arm 303 is manually movable by a medical person (operator). The display 400 is capable of displaying a radiographic fluoroscopic image captured by the radiographic imaging apparatus 300, and a radiographic image captured by the radiographic imaging apparatus 300.

(Effects of One or More Embodiments)

According to one or more embodiments, effects as described below can be obtained.

As described above, in one or more embodiments, it is provided that the operation controller 51 (61) that causes the display 52 (62) to display an elapsed time in the tilted posture in a condition in which the table 1 is put in a tilted posture. In a condition in which the table 1 is put in a tilted posture, the controller 3 or the operation controller 51 (61) causes the display 400 to display an elapsed time in the tilted posture. Accordingly, a medical person such as a surgeon, an assistant, a nurse, or a medical technician can easily know an elapsed time since the table 1 is put in a tilted state by checking the elapsed time displayed by the display 52 (62) or the display 400. As a result, the medical person can pay attention not to hold the patient 10 placed on the table 1 in the same tilted posture for a long time, thereby preventing start or degradation of decubitus (bedsore) of the patient 10 when the patient 10 is tilted by tilting the table 1.

In one or more embodiments, as described above, the operation controller 51 (61) causes the display 52 (62) or the display 400 to display posture information of the table 1. The controller 3 causes the display 400 to display posture information of the table 1. With this configuration, a medical person can easily know the tilt of the table 1 and thus the tilted state of the patient 10. As a result, the medical person can pay attention not to hold the patient 10 in the same tilted posture for a long time, thereby effectively preventing start or degradation of decubitus (bedsore) of the patient 10. When it is unable to directly check the posture of the table 1 because the patient 10 placed on the table 1 is covered by a surgical cover during a surgical operation or the like, the medical person can easily know the posture of the table 1 by checking posture information of the table 1 on the display 52 (62) or the display 400.

In one or more embodiments, as described above, the display 52 (62) displays, as posture information of the table 1, a diagram (illustration) representing the posture of the table 1. With this configuration, since the diagram (illustration) representing the posture of the table 1 is displayed on the display 52 (62), a medical person (user) can easily know the posture of the table 1, i.e., whether the table 1 is tilted or not, for example. As a result, knowing that the table 1 is tilted, the medical person can easily recognize that decubitus (bedsore) potentially occurs to the patient 10.

In one or more embodiments, as described above, the display 52 (62) displays the tilt angle of the table 1 with respect to the horizontal plane as posture information of the table 1. With this configuration, a medical person (user) can easily know the degree of tilt of the table 1 by referring to the tilt angle displayed on the display 52 (62).

In one or more embodiments, as described above, the display 52 (62) displays, as posture information of the table 1, a diagram (illustration) including arrows indicating the directions of rotation of the table 1 with respect to the horizontal plane and the tilt angle of the table 1 with respect to the horizontal plane. With this configuration, a medical person (user) can easily know the direction and degree of tilt of the table 1 by referring to the diagram (illustration) and tilt angle displayed on the display 52 (62).

In one or more embodiments, as described above, the mode setting unit 55 (65) is capable of setting, as an operation mode to change the posture of the table 1, the roll mode in which the table 1 is rotated about an axis parallel to the longitudinal direction (X direction) of the table 1, and the pitch mode in which the table 1 is rotated about an axis parallel to the transverse direction (Y direction) of the table 1. With this configuration, the table 1 can be easily tilted through selection of a mode by the mode setting unit 55 (65).

In one or more embodiments, as described above, the position of the rotation center is selectable from among positions in the longitudinal direction (X direction) of the table 1 in the pitch mode. With this configuration, the vicinity of the head of the patient 10, the vicinity of the abdominal part thereof, and the vicinity of the leg part thereof can be selected as the position of the rotation center, and thus the posture of the patient 10 can be easily changed in accordance with a situation.

In one or more embodiments, as described above, the mode setting unit 55 (65) is capable of setting, as an operation mode to change the posture of the table 1, the vertical movement mode in which the table 1 is vertically moved. In a condition in which the vertical movement mode is set, the operation controller 51 (61) causes the display 52 (62) to display, as posture information of the table 1, a diagram (illustration) including arrows indicating the directions of the vertical movement of the table 1 and the height of the table 1 from the floor surface. With this configuration, the table 1 can be easily moved in the vertical direction (Z direction) through selection of a mode by the mode setting unit 55 (65). In addition, a medical person (user) can easily know whether the table 1 is moving upward or downward and at which height the table 1 is positioned by referring to the diagram (illustration) and height displayed on the display 52 (62).

In one or more embodiments, as described above, the mode setting unit 55 (65) is capable of setting, as an operation mode to change the posture of the table 1, the yaw mode in which the table 1 is rotated about a rotation axis extending in the vertical direction (Z direction) in the horizontal plane. In a condition in which the yaw mode is set, the operation controller 51 (61) causes the display 52 (62) to display, as posture information of the table 1, a diagram (illustration) including arrows indicating the directions of rotation of the table 1 with respect to a reference position and the angle of the table 1 with respect to the reference position. With this configuration, the table 1 can be easily rotated in the horizontal plane through selection of a mode by the mode setting unit 55 (65). In addition, a medical person (user) can easily know which direction and how much the table 1 is rotated by referring to the diagram (illustration) and angle displayed on the display 52 (62).

In one or more embodiments, as described above, the position of the rotation center is selectable from among positions in the longitudinal direction (X direction) of the table 1 in the yaw mode. With this configuration, the vicinity of the head of the patient 10, the vicinity of the abdominal part thereof, and the vicinity of the leg part thereof can be selected as the position of the rotation center, and thus the posture of the patient 10 can be easily changed in accordance with a situation.

In one or more embodiments, as described above, the mode setting unit 55 (65) is capable of setting, as an operation mode to change the posture of the table 1, the horizontal movement mode in which the table 1 is linearly moved in the horizontal plane. In a condition in which the horizontal movement mode is set, the operation controller 51 (61) causes the display 52 (62) to display, as posture information of the table 1, a diagram (illustration) including arrows indicating the moving direction of the table 1. With this configuration, the table 1 can be easily moved in the horizontal direction through selection of a mode by the mode setting unit 55 (65). In addition, a medical person (user) can easily know which direction the table 1 is moving by referring to the diagram (illustration) displayed on the display 52 (62).

In one or more embodiments, as described above, the operating table 100 includes the robotic arm 2 including one end supported on the base 21 and an opposite end supporting the table 1. With this configuration, the table 1 can be moved by the robotic arm 2, and thus the movement range and freedom of the table 1 can be increased as compared to the case where the table 1 is moved by a base fixed to the floor. In addition, the movement and posture change of the table 1 can be easily performed with the robotic arm 2.

In one or more embodiments, as described above, the robotic arm 2 includes the motor 41 and the electromagnetic brake 43, and counting of an elapsed time in the tilted posture is started when actuation of the motor 41 is stopped with the table 1 put in a tilted state and the electromagnetic brake 43 is actuated. This configuration is capable of counting an elapsed time since the robotic arm 2 stops driving, and thus counting an elapsed time since the table 1 is tilted and completely stopped.

In one or more embodiments, as described above, the controller 3 performs control to move the table 1 while at least one of the move direction receivers 63a is operated. With this configuration, the table 1 is moved only while at least one of the move direction receivers 63a is operated, and thus only the operation of the move direction receivers 63a just has to be stopped to stop movement of the table 1. Accordingly, the movement of the table 1 can be stopped reliably and immediately.

In one or more embodiments, as described above, the controller 3 performs control to move the table 1 while the joystick 53a is operated. With this configuration, the table 1 is moved only while the joystick 53a is operated, and thus only the operation of the joystick 53a just has to be stopped to stop movement of the table 1. Accordingly, the movement of the table 1 can be stopped reliably and immediately.

In one or more embodiments, as described above, the controller 3 performs control to move the table 1 while the trigger unit 54 (64) and the move operation receiving unit 53 (63) are operated together. Specifically, when the trigger unit 54 (64) is operated, the motor 41 is energized, and braking of the motor 41 by the electromagnetic brake 43 is canceled. As a result, only while the trigger unit 54 (64) is operated, the operation of the move operation receiving unit 53 (63) is enabled, so that the table 1 can be moved. Accordingly, when the move operation receiving unit 53 (63) is unintentionally operated, the table 1 is not moved unless the trigger unit 54 (64) is operated. Accordingly, unintentional movement of the table 1 can be prevented.

In one or more embodiments, as described above, the robotic arm 2 includes one end supported on the base 21 to be rotatable about the axis extending in the vertical direction (Z direction) and the opposite end supporting the table 1 at a position adjacent to the one end of the table 1 in the longitudinal direction (X direction), and has at least six degrees of freedom to move the table 1. With this configuration, the table 1 can be easily moved to a desired position by the robotic arm 2 having at least six degrees of freedom. In addition, the movement range and freedom of the table 1 on which to place the patient 10 can be effectively increased by the robotic arm 2 having at least six degrees of freedom.

In one or more embodiments, as described above, the table 1 includes the radiolucent part 11 and the support unit 12 supporting the radiolucent part 11, and the opposite end of the robotic arm 2 supports the support unit 12 of the table 1. With this configuration, when the robotic arm 2 is disposed close to the support unit 12 to provide a sufficient space below the radiolucent part 11, a device for performing radiographic imaging can be placed below the radiolucent part 11 to perform radiographic imaging on the patient 10 being placed on the table 1.

(Modification)

The embodiments disclosed herein should be considered exemplary in all aspects, non-exhaustive and not limiting. The scope of the present invention is indicated by the claims rather than the explanation of the above embodiments and also embraces all changes that come within the meaning and range of equivalents of the claims.

For example, in the above-described embodiments, a hybrid operation room system may include a radiographic imaging apparatus. Additional or alternative embodiments may not be limited to such examples. For example, the hybrid operation room system may include a magnetic resonance imaging apparatus that captures a magnetic resonance image of a patient. Alternatively, the hybrid operation room system may include both of a radiographic imaging apparatus and a magnetic resonance imaging apparatus.

In the above-described embodiments, a robotic operating table is provided in a hybrid operation room. Additional or alternative embodiments may not be limited to such examples. For example, the robotic operating table may be provided in an operation room other than the hybrid operation room.

In the above-described embodiments, the robotic operating table is provided with two operation devices. Additional or alternative embodiments may not be limited to such examples. For example, the robotic operating table may be provided with one operation device or may be provided with three operation devices or more.

In the above-described embodiments, an operation device is connected with a controller through wired communication. Additional or alternative embodiments may not be limited to such examples. For example, the operation device may be connected with the controller through wireless communication.

In the above-described embodiments, the movement and posture change of the table of the operating table are performed by an articulated robotic arm. Additional or alternative embodiments may not be limited to such examples. For example, the movement and posture change of the table of the operating table may be performed by any device other than the articulated robotic arm.

Figure 8:
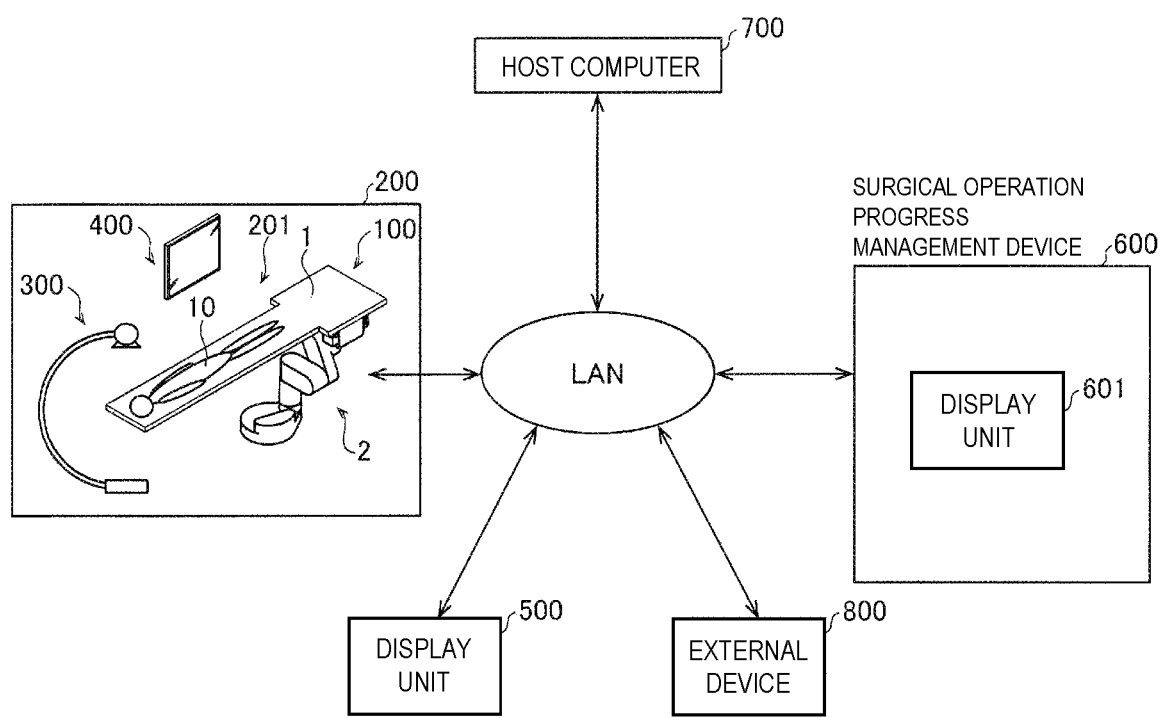
FIG. 8 is a diagram illustrating a display according to a modification of one or more embodiments.

In the above-described embodiments, a display is provided to an operation device. Additional or alternative embodiments may not be limited to such examples. For example, the display may be provided separately from the operation device. For example, in a modification illustrated in FIG. 8, a display provided outside an operation room may display, for example, the state of a table, the state of an operation of an operation device, and an operation screen. Specifically, as illustrated in FIG. 8, the state of the table and the like may be displayed on a display 500 provided outside the hybrid operation room 200 and connected with a local area network (LAN) inside a hospital in which the hybrid operation room 200 is provided. The display 500 may be provided at, for example, a nurse station. In a condition in which a surgical operation progress management device 600 for managing the progress of a surgical operation may be provided outside of the hybrid operation room 200, the state of the table and the like may be displayed on a display 601 of the surgical operation progress management device 600. The display 601 of the surgical operation progress management device 600 may be provided at, for example, a control center adjacent to the hybrid operation room 200. For example, a host computer 700 and an external device 800 such as a portable terminal owned by hospital staff may be connected with the LAN inside the hospital.

In the above-described embodiments, a mode setting unit and a move operation receiving unit have background colors different from each other. Additional or alternative embodiments may not be limited to such examples. For example, the mode setting unit and the move operation receiving unit may provide touch feelings or textures different from each other. For example, the surfaces of the mode setting unit and the move operation receiving unit may have uneven shapes different from each other.

In the above-described embodiments, a horizontal articulated assembly includes three horizontal joints. Additional or alternative embodiments may not be limited to such examples. For example, the horizontal articulated assembly may include two horizontal joints or may include four horizontal joints or more.

In the above-described embodiments, a vertical articulated assembly includes three vertical joints. Additional or alternative embodiments may not be limited to such examples. For example, the vertical articulated assembly may include two vertical joints or may include four vertical joints or more.

In the above-described embodiments, an articulated robotic arm includes three horizontal joints in a series and three vertical joints in a series. Additional or alternative embodiments may not be limited to such examples. For example, the articulated robotic arm may be a vertical articulated robot including parts at which rotation axes of joints adjacent to each other are orthogonal to each other.

In the above-described embodiments, the articulated robotic arm has the seven degrees of freedom. Additional or alternative embodiments may not be limited to such examples. For example, the articulated robotic arm may have six or less degrees of freedom or eight or more degrees of freedom, but preferably may have at least six degrees of freedom.

In the above-described embodiments, a base is buried and fixed in the floor. Additional or alternative embodiments may not be limited to such examples. For example, the base may be fixed on the floor.

In the above-described embodiments, the controller 3 is disposed in the base 21. Additional or alternative embodiments may not be limited to such examples. For example, the controller 3 may be housed in a control box, and the control box may be disposed at an optional position inside the hybrid operation room 200 or the control center adjacent to the hybrid operation room 200.

In the above-described embodiments, the controller 3 performs control to stop movement of the table 1 by invalidating the operation of the move operation receiving unit 53 (63) when the table 1 arrives at a preset position, and to stop energization of the motor 41 and actuate the electromagnetic brake 43 when the operation of the trigger unit 54 (64) is stopped by a user. Additional or alternative embodiments may not be limited to such examples. For example, when the table 1 arrives at a preset position, the controller 3 may stop energization of the motor 41 and actuate the electromagnetic brake 43 even though the move operation receiving unit 53 (63) and the trigger unit 54 (64) are operated together.

The operating table and the operation device as disclosed in EP1028684B1 are capable of tilting a patient by changing the tilt of the table on which to place the patient, but do not allow a medical person performing a surgical operation to know how long the patient is held on the tilted table.

One or more embodiments described above provide an operating table operation device and an operating table that allow, when a patient is tilted by tilting a table, a medical person to easily know an elapsed time since the table is put in the tilted state.

The above-described aspects may be combined with each other as practicable within the contemplated scope of embodiments. The above described embodiments are to be considered in all respects as illustrative, and not restrictive. The illustrated and described embodiments may be extended to encompass other embodiments in addition to those specifically described above without departing from the intended scope of the invention. The scope of the invention is to be determined by the appended claims when read in light of the specification including equivalents, rather than solely by the foregoing description. Thus, all configurations including configurations that fall within equivalent arrangements of the claims are intended to be embraced in the invention.

What is claimed is:

1. An operation device for operating movement of a patient placement table of an operating table, the patient placement table being on which a patient can be placed, the operating table comprising a motor to move the patient placement table and an electromagnetic brake to prevent move of the patient placement table, the operation device comprising:
    a display;
    a move operation receiving unit that receives, a user move operation to move the patient placement table; and
    an operation controller,
    wherein, in a condition in which the patient placement table is put in a tilted posture in accordance with the move operation, the operation controller, in response to actuation of the motor being stopped and the electromagnetic brake being actuated, starts counting an elapsed time in the tilted posture and causes the display to display the elapsed time in the tilted posture.

2. The operation device according to claim 1, wherein the operation controller causes the display to display posture information of the patient placement table.

3. The operation device according to claim 2, wherein the posture information of the patient placement table comprises a diagram representing a posture of the patient placement table.

4. The operation device according to claim 2, wherein the posture information of the patient placement table comprises a tilt angle of the patient placement table with respect to a horizontal plane.

5. The operation device according to claim 2, wherein the posture information of the patient placement table comprises an arrow indicating a direction of rotation of the patient placement table with respect to a horizontal plane, and a tilt angle of the patient placement table with respect to the horizontal plane.

6. The operation device according to claim 1, further comprising a mode setting unit that sets an operation mode in which a posture of the patient placement table is changed, wherein
the operation mode comprises:
a roll mode in which the patient placement table is rotated about a rotation axis parallel to a longitudinal direction of the patient placement table, and
a pitch mode in which the patient placement table is rotated about a rotation axis parallel to a transverse direction of the patient placement table.

7. The operation device according to claim 6, wherein, in the pitch mode, the rotation axis is selectable from a plurality of axes located along the longitudinal direction of the patient placement table.

8. The operation device according to claim 1, further comprising a mode setting unit that sets an operation mode in which a posture of the patient placement table is changed, wherein
the operation mode comprises a vertical movement mode in which the patient placement table is vertically moved, and
in a condition in which the vertical movement mode is set, the posture information of the patient placement table displayed on the display comprises an arrow indicating a direction of vertical movement of the patient placement table, and a height of the patient placement table from a floor surface.

9. The operation device according to claim 1, further comprising a mode setting unit that sets an operation mode in which a posture of the patient placement table is changed, wherein
the operation mode comprises a yaw mode in which the patient placement table is rotated in a horizontal plane about a rotation axis extending in a vertical direction, and
in a condition in which the yaw mode is set, the posture information of the patient placement table displayed on the display comprises an arrow indicating a direction of rotation of the patient placement table with respect to a reference position, and an angle of the patient placement table with respect to the reference position.

10. The operation device according to claim 9, wherein, in the yaw mode, the rotation axis is selectable from a plurality of predetermined axes.

11. The operation device according to claim 1, further comprising a mode setting unit that sets an operation mode in which a posture of the patient placement table is changed, wherein
the operation mode comprises a horizontal movement mode in which the patient placement table is linearly moved in a horizontal plane, and
in a condition in which the horizontal movement mode is set, the posture information of the patient placement table displayed on the display comprises an arrow indicating a moving direction of the patient placement table.

12. The operation device according to claim 1, wherein the operating table comprises an articulated robotic arm comprising a plurality of joints, and including a first end supported on a base and a second end supporting the patient placement table.

13. An operating table comprising:
a patient placement table on which a patient can be placed;
a movement mechanism that comprises a motor and an electromagnetic brake and moves the patient placement table;
an operation device comprising a move operation receiving unit that receives a user move operation to move the patient placement table;
a display; and
a controller that controls the movement mechanism in accordance with the move operation received by the move operation receiving unit,
wherein, in a condition in which the patient placement table is put in a tilted posture in accordance with the move operation, the controller, in response to actuation of the motor being stopped and the electromagnetic brake being actuated, starts counting an elapsed time in the tilted posture and causes the display to display the elapsed time in the tilted posture.

14. The operating table according to claim 13, wherein the controller causes the display to display posture information of the patient placement table.

15. The operating table according to claim 13, wherein the posture information of the patient placement table displayed on the display comprises at least one of:
an arrow indicating a direction of rotation of the patient placement table with respect to a horizontal plane; and
the tilt angle of the patient placement table with respect to the horizontal plane.

16. The operating table according to claim 13, wherein
the operation device comprises an operation controller and an operation display, and
in a condition in which the patient placement table is put in the tilted posture, the operation controller causes the operation display to display an elapsed time in the tilted posture.

17. The operating table according to claim 13, wherein
the operation device further comprises a mode setting unit that sets an operation mode in which a posture of the patient placement table is changed, and
the operation mode comprises:
a roll mode in which the patient placement table is rotated about an axis parallel to a longitudinal direction of the patient placement table; and
a pitch mode in which the patient placement table is rotated about an axis parallel to a transverse direction of the patient placement table.

18. The operating table according to claim 13, wherein
the move operation receiving unit comprises move direction receivers provided respectively for directions in which the patient placement table is moved, and the controller causes the movement mechanism to move the patient placement table while at least one of the move direction receivers is operated.

19. The operating table according to claim 13, wherein the move operation receiving unit comprises a joystick, and the controller causes the movement mechanism to move the patient placement table while the joystick is operated.

20. The operating table according to claim 13, wherein the operation device comprises a trigger unit that enables operation of the move operation receiving unit, and the controller causes the movement mechanism to move the patient placement table while the trigger unit and the move operation receiving unit are operated together.

21. The operating table according to claim 13, wherein the operation device comprises a trigger unit, the movement mechanism comprises joints, each of the joints comprises the motor and the electromagnetic brake, and the controller, while the trigger unit is not operated, performs control that stops energization of the motor and actuates the electromagnetic brake, and the controller, while the trigger unit is operated, performs control that energizes the motor and does not actuate the electromagnetic brake.

22. The operating table according to claim 13, wherein the movement mechanism comprises an articulated robotic arm comprising a plurality of joints, and including a first end supported on a base and a second end supporting the patient placement table.

23. The operating table according to claim 22, wherein the first end of the robotic arm is supported on the base to be rotatable about an axis extending in a vertical direction, the second end of the robotic arm supports the patient placement table at a position adjacent to an end in a longitudinal direction of the patient placement table, and the robotic arm moves the patient placement table with at least six degrees of freedom.

24. The operating table according to claim 23, wherein the patient placement table includes a radiolucent part and a support unit supporting the radiolucent part, and the second end of the articulated robotic arm supports the support unit of the patient placement table.

\* \* \* \* \*